United States Patent [19]

Torck et al.

[11] 4,024,203

[45] May 17, 1977

[54] OLIGOMERIZATION OF UNSATURATED HYDROCARBONS WITH ACID CATALYSTS

[75] Inventors: Bernard Torck, Chatou; Georges Vidouta, Neuilly sur Seine; Peirre Pariot, Colombes; Michel Hellin, Andresy, all of France

[73] Assignee: Institut Francais du Petrole, Rueil-Malmaison, France

[22] Filed: Jan. 16, 1976

[21] Appl. No.: 649,845

Related U.S. Application Data

[60] Continuation of Ser. No. 319,610, Dec. 29, 1972, abandoned, which is a continuation-in-part of Ser. No. 277,084, Aug. 1, 1972, abandoned, which is a division of Ser. No. 89,462, Nov. 13, 1970, abandoned.

[30] Foreign Application Priority Data

Nov. 24, 1969 France .............................. 69.40466

[52] U.S. Cl. ...................................... 260/683.15 A
[51] Int. Cl.$^2$ ...................... C07C 3/12; C07C 3/14
[58] Field of Search ......... 260/683.15 R, 683.15 A, 260/683.15 B

[56] References Cited

UNITED STATES PATENTS

| | | | |
|---|---|---|---|
| 2,085,535 | 6/1937 | Langedijk et al. | 260/683.15 B |
| 2,142,980 | 1/1939 | Huijser et al. | 260/683.15 B |
| 2,320,256 | 5/1943 | Bailey et al. | 260/683.15 B |
| 3,354,236 | 11/1967 | Klein | 260/683.15 B |
| 3,732,328 | 5/1973 | Wright | 260/680 B |

OTHER PUBLICATIONS

Olah, Friedel–Crafts & Related Reactions, vol. 1, pp. 205–213, (1963).

*Primary Examiner*—D. Horwitz
*Attorney, Agent, or Firm*—Millen & White

[57] ABSTRACT

For polymerizing unsaturated hydrocarbons into oligomers with acid catalysts, there are employed liquid catalyst compositions containing a Bronsted acid and a sulfone of formula R—SO$_2$—R', wherein R and R' are each separately a monovalent radical containing from 1 to 8 carbon atoms or form together a divalent radical having from 3 to 12 carbon atoms, the acid concentration being at least 10$^{-5}$ moles per liter of sulfone and at most the saturation concentration without exceeding 5 moles per liter of sulfone. The catalysts may be dispersed in an inert hydrocarbon solvent and Lewis acids may also be added.

14 Claims, No Drawings

OLIGOMERIZATION OF UNSATURATED HYDROCARBONS WITH ACID CATALYSTS

This is a continuation of application Ser. No. 319,610, filed Dec. 29, 1972, which is a continuation-in-part application of Ser. No. 277,084, filed Aug. 1, 1972, which is a divisional application of Ser. No. 89,462, filed Nov. 13, 1970, all of said applications now being abandoned.

This invention relates to the use of acidic catalyst compositions in such reactions as oligomerization and polymerization of unsaturated hydrocarbons.

Up to now, these reactions have been carried out either in the liquid phase, in the presence of a strong inorganic acid such as concentrated sulfuric acid, anhydrous hydrofluoric acid with or without addition of a Lewis acid such as $BF_3$ or $SbF_5$, or in the presence of aluminium chloride, or in the vapor phase in the presence of the acid catalysts of the solid phosphoric acid type. In both cases, the catalysts suffer from the major drawback of being consumed in substantial amounts. Thus, in the liquid phase, there are formed acid muds by reaction of the feed with the catalyst. These acid muds, which are insoluble, are quickly deactivated, and this results in a substantial loss of catalyst. These acid muds further constitute a catalyst, the catalytic activity of which cannot be controlled easily. In the vapor phase, the solid phosphoric acids are quickly deactivated and desegregated. They must therefore be replaced after relatively short periods of use.

The acid catalyst compositions of this invention do not suffer, or only to a decreased extent from such disadvantages. These catalyst compositions are constituted by known acid catalysts, conventionally used for carrying out such reactions, in solution in a solvent consisting of a sulfone or a sulfone mixture. The solubilization of these catalysts in solvents such as sulfones offers the advantage of producing very acid solutions at relatively low concentrations. By way of example, when sulfuric acid is dissolved in tetramethylene sulfone, in a proportion of 5% by weight, there is obtained a solution, the acidity of which is similar to that of a mixture of water and sulfuric acid having a 60% by weight content of the latter. Besides, the Bronsted acids are generally very soluble in these solvents and this results in the formation of a low amount of acid muds and accordingly in an increased life time of the catalyst dissolved therein. Finally, the fact that there is obtained a perfectly homogeneous solution is a very significant advantage for controlling the activity of the catalyst.

It is known that these sulfones are good solvents for the aromatic hydrocarbons, but they are poor solvents for aliphatic hydrocarbons, and there is accordingly an advantage in the use of acid catalytic solutions in two liquid phase systems for continuous industrial operations. The catalyst compositions according to the invention are particularly suitable for the manufacture of hydrocarbons of high antiknock characteristics by polymerization of olefins.

The order of reactivity of the unsaturated aliphatic hydrocarbons is as follows:

tertiary > secondary > primary.

As a result thereof the catalyst composition is perfectly adapted to the selective extraction of tertiary olefins from an olefin mixture. This catalyst composition may thus be used, for example, for selectively extracting isobutene from a steam cracking $C_4$ cut and methylbutenes from a steam cracking $C_5$ cut.

In view of the very low solubility of the aliphatic hydrocarbons in such catalytic solutions, the olefinic hydrocarbons are converted to oligomers having an oligomerization degree which may be adjusted at will as a function of the operating conditions. The higher the oligomerization degree, the greater the settling of the oligomer.

The oligomerization degree may be adjusted by acting on various parameters such as the reaction temperature, the contact time, the acid concentration or the extraction by a third solvent insoluble in the sulfones such as, for example, cyclohexane or any other aliphatic, cyclic or alicyclic saturated hydrocarbon which cannot react. It is thus possible, in many cases, to selectively produce the olefin dimer. By way of example, the use of a third solvent or of a small concentration of acid catalyst favors the dimer formation. However, it is also possible to convert the olefins to higher oligomers which may constitute oil additives or which can be used as a base for the synthesis thereof, for example, by increasing the contact time.

Digressing somewhat, it is to be noted that as far as the alkylation of aromatic hydrocarbons by means of olefins is concerned, the selectivity to monoalkylates is the higher as the molecular weight of the olefin is the higher. It can be seen from the following Examples 18,19 and 20 relating to the alkylation of benzene by means of propylene, that the selectivity is relatively small due to the formation, during the course of the reaction, not only of the di-, tri- and tetra-isopropylbenzenes, but also of propylene oligomers. On the contrary, when the olefin has a relatively high molecular weight, the alkylbenzene selectivity is very high and the secondary reaction of olefin oligomerization is practically negligible (Examples 21 and 22). Accordingly, the converse is also true — lower olefins, e.g., propylene and butylene, form oligomers quite readily.

The catalysts which may be dissolved in the sulfones for obtaining these catalyst compositions are Bronsted acids, such as, for example, sulfuric acid, fluorosulfuric acid, the sulfonic acids of the $R-SO_3H$ type in which R is an alkyl group, an aromatic group or a halogenated alkyl or aromatic group, the hydrogen halides, the acids of the formula $X_nPO_2H(OR)_{2-n}$ wherein X is a halogen, R is either H or an alkyl group and $n$ is 0, 1 or 2, or $CX_nH_{3-n}COOH$ wherein X is a halogen and $n$ is 0, 1, 2 or 3.

Lewis acids may be added in addition, but not in place of, the Bronsted acids. Preferred Lewis acids are those of the formula $R_nMX_{x-n}$, wherein R is an alkyl, cycloalkyl, alkoxy or aryl group, these groups being optionally halogenated, X is a halogen or any other electronegative group such as, for example, $SO_3F$, and M is a metal atom, $x$ being advantageously the higher valence of the metal atom and $n$ having a value from 0 to $x$. Especially preferred are those Lewis acids whose metal is chosen from the groups III, IV, and V of the periodic classification of the elements and is more particularly B, Al, Ga, In, Sn, Ti, Zr, P, As, Sb, Bi, V, Nb or Ta, the invention being however not limited to these groups since such compounds as, for example, $BeX_2$, $CuX_2$, $ZnX_2$, $CdX_2$, $HgX_2$, $FeX_3$, $MoX_6$, $WX_6$ and $UF_6$ are also very active in these catalyst compositions. The most suitable halogen in these Lewis acids is fluorine, and the metal fluorides which are used most advantageously are $SbF_5$, $TaF_5$, $PF_5$ $NbF_5$, $BF_3$, $SnF_4$, $AlF_3$ and $TiF_4$. However, the Lewis acids are not limited to the metal fluorides since other metal halides such as, for instance, $AlCl_3$, $SnCl_4$ or $AlBr_3$, may also be used in solution in the sulfones. As will be seen from the examples, the combination of Bronsted and Lewis acids results in catalysts which are particularly active.

The sulfones which may be used to dissolve said acid catalysts and thus form said new acid catalyst compositions are the sulfones of the general formula $$R-SO_2-R'$$

wherein R and R' are monovalent hydrocarbon radicals, each containing from 1 to 8 carbon atoms, particularly alkyl or aryl radicals, such as, for example, dimethylsulfone, di n-propylsulfone, diphenylsulfone and ethylmethylsulfone, and the alicyclic sulfones wherein the $SO_2$ group is inside a hydrocarbon ring. In such a case, R and R' are forming together a branched or unbranched hydrocarbon divalent radical preferably containing from 3 to 12 carbon atoms. Among the latter, tetramethylenesulfone or sulfolane, 3 methylsulfolane and 2,4-dimethyl-sulfolane are more particularly suitable since they offer the advantage of being liquid at room temperature. These sulfones may also have substituents, particularly one or more halogen atoms, such as, for example, chloromethylethylsulfone. These sulfones may advantageously be used in the form of mixtures.

In the catalyst composition according to the invention, the acid concentration is advantageously between $10^{-5}$ moles per liter of sulfone and the concentration corresponding to the saturation without, however, exceeding 5 moles per liter of sulfone. The catalyst according to the invention may be used at temperatures between $-20°$ and $200°$ C, and at pressures ranging from 0.1 to 200 atmospheres. When there is used a Lewis acid, in the presence of a cocatalyst, the molar ratio between the Lewis acid and the cocatalyst may vary between 0.01/1 and 200/1 and preferably 0.1/1 and 10/1. It is advantageous to stir the reaction mixture.

It is desirable that the hydrocarbon feed be dehydrated, since the accumulation of water in the catalytic solution would result in the deactivation thereof.

In order to prevent such possible problems, there can be dissolved in the catalytic solution a dehydrating agent such as, for example, phosphoric anhydride, which not only has no detrimental effect on the catalyst properties, but in some cases, improves them substantially.

EXAMPLE 1

A solution of 5g of 100% sulfuric acid in 250 g of tetramethylenesulfone is heated up to 40° C and stirred with a stirrer operated at 2,700 runs per minute. Isobutene is introduced continuously into the reactor at atmospheric pressure. The oligomers, as formed, progressively separate from the catalytic solution. After 1 hour the stirring is stopped and the oligomers settle in less than 1 minute. There are thus recovered 18 g of oligomers. These oligomers contain 50% by weight of dimers and 30% by weight of trimers in addition to the dissolved isobutene.

EXAMPLES 2 TO 12

These examples relate to experiments which are carried out in the same conditions as in Example 1 except for the catalyst.

The catalysts consist of various metal halides associated with a cocatalyst which, according to the case, may be water, hydrofluoric acid or phosphoric acid. The results given in the following table show the influence of the metal halide, and, in the case of $BF_3$, of the cocatalyst on the catalytic activity of the tetramethylenesulfone solution. The obtained oligomers contain from 40 to 70% by weight of dimers and 20 to 40% by weight of trimers.

| Example No | Metal halide | Cocatalyst | Concentration* | Oligomer g/h/g of metal halide |
|---|---|---|---|---|
| 2 | $WF_6$ | $H_2O$ | 0.06 | 65 |
| 3 | $SnCl_4$ | HF | 0.2 | 72 |
| 4 | $TiF_4$ | HF | 0.2 | 140 |
| 5 | $AlF_3$ | HF | 0.1 | 270 |
| 6 | $SnF_4$ | HF | 0.05 | 290 |
| 7 | $BF_3$ | $H_3PO_4$ | 0.18 | 90 |
| 8 | $BF_3$ | $H_2O$ | 0.01 | 350 |
| 9 | $BF_3$ | HF | 0.01 | 450 |
| 10 | $TaF_5$ | $H_2O$ | 0.015 | 470 |
| 11 | $PF_5$ | HF | 0.1 | 600 |
| 12 | $SbF_5$ | HF | 0.005 | 4800 |

*Molar concentration per liter of each of the catalyst elements (metal halide and cocatalyst).

EXAMPLE 13

A solution of 0.4 g of $BF_3-O(C_2H_5)_2$ in 125 g of tetramethylenesulfone is used under the same conditions as in the preceding examples. After 1 hour, there are recovered 66 g of oligomers containing 51% of dimers and 32% of trimers. This is a comparative experiment and not part of the presently claimed invention.

EXAMPLE 14

This example shows the influence of a third solvent on the selectivity to dimers in the oligomerization of isobutene. 80 cc of tetramethylenesulfone containing $BF_3$ and HF at individual concentrations of 6.5, $10^{-3}$ moles per liter and 80 cc of decahydronaphthalene containing 5 g of isobutene are introduced into a reaction vessel. Both solutions are heated up to 40° C and stirred with a stirrer operated at 2,500 runs per minute.

As a function of time, there are observed the consumption of isobutene and the formation of dimers and trimers in the hydrocarbon phase. After 1 hour, the conversion rate of isobutene amounts to 45% and the molar ratio dimers/trimers is 16.

EXAMPLES 15, 16, AND 17

These examples show the possibility of using the catalyst compositions of this invention for selectively extracting tertiary olefins from a mixture of primary, secondary, and tertiary olefins. The present case is concerned with the extraction of isobutene from a steam cracking $C_4$ cut. The reaction is carried out under a total pressure of 4 kg/cm², so as to maintain the $C_4$ cut in the liquid phase. The acid solution in tetramethylenesulfone and the $C_4$ cut are heated up to 40° C and stirred with a stirrer operated at 1,800 runs per minute.

The ratio by liquid volume of the $C_4$ cut to the catalytic solution is 1. The composition of the $C_4$ cut in percent by weight is as follows: propane and propylene : 0.6%; isobutane : 1.7%; n-butane 5.6%; isobutene 53.1%; 1-butene : 29.1%; trans 2-butene : 5.1%; cis 2-butene : 3.2%; butadiene : 1.6%. The following table indicates the acid which has been dissolved into the sulfone and its concentration in moles per liter, the reaction time, the conversion rates of isobutene and of the three n-butenes, and finally, the composition of the obtained oligomers free from volatile hydrocarbons.

| Ex. No | Catalyst and concentration (mol.liter$^{-1}$) | | Reaction times in hours | Conversion rate | % | Composition of the gasoline dimers % by weight | trimers % by weight |
|---|---|---|---|---|---|---|---|
| 15 | BF$_3$ HF | 0.006 0.006 | 5.0 | isobutene n-butenes | 78 1.8 | 83 | 12 |
| 16 | BF$_3$ HF | 0.03 0.02 | 0.5 | isobutene n-butenes | 91.4 5.3 | 64 | 18 |
| 17 | SbF$_5$ HF | 0.0025 0.0035 | 2.0 | isobutene n-butenes | 95 5.5 | 67 | 24 |

EXAMPLE 18

This example relates to the alkylation of benzene by means of propylene. There are introduced into a reactor 150 g of a mixture of tetramethylenesulfone and benzene (15 g) containing boron trifluoride and phosphoric acid at individual concentrations of 0.2 mole per liter, and the resulting mixture is heated up to 40° C and stirred at 2,700 runs per minute. Propylene is continuously introduced at the atmospheric pressure. The propylene absorption velocity is substantially constant and equal to 0.15 mole per hour. After 3 hours, the stirring is discontinued and there are settled 16 g of organic phase containing mono-, di-, tri-, and tetraisopropylbenzenes.

EXAMPLE 19

There are reacted in the same conditions as in Example 20, 150 g of a mixture of tetramethylenesulfone and benzene (15 g) containing antimony pentafluoride and hydrofluoric acid at the respective concentrations of 0.1 and 0.05 mole per liter. The propylene absorption velocity is 1.1 mole per hour. The organic phase which settles, contains mono-, di-, tri- and tetraisopropylbenzenes.

EXAMPLE 20

There are introduced 100 cc of a solution of BF$_3$ and HF in sulfolane at the individual concentration of 0.1 mol per liter, and 10 g of benzene, into a reaction vessel. The whole is heated up to 40° C and stirred with a stirrer operated at 2,700 runs per minute. Propylene is introduced continuously at atmospheric pressure. The propylene absorption velocity is substantially constant and is equal to 0.15 mole per hour. After 2 hours, stirring is discontinued and there are settled 11 g of hydrocarbon products, containing 18% by weight of propylene oligomers and 82% of compounds containing the benzene ring. The composition of the aromatic products, obtained by chromatographic determination, is as follows:

| | % mol |
|---|---|
| benzene | 60 |
| cumene | 26 |
| diisopropylbenzenes | 9.3 |
| triisopropylbenzenes | 4.0 |
| tetraisopropylbenzenes | 0.7 |

The molar selectivity of cumene with respect to the consumed propylene, calculated by taking into account the products remaining in the catalytic phase, is 20%.

EXAMPLE 21

There are introduced 50 cc of a solution of BF$_3$ and HF in sulfolane at the respective concentrations of 1.5 and 2.5 mole per liter and a mixture of 39 g of benzene and 16.8 g of 1-dodecene into a reaction vessel. The reaction is conducted at 40° C and at atmospheric pressure. The whole mixture is emulsified by means of a stirrer operated at 2,700 runs per minute. After 2 hours of reaction, stirring is discontinued. The hydrocarbon supernatant phase is withdrawn. The same operation is repeated twice (there are introduced) at each time 39 g of benzene and 16.8 g of 1-dodecene) by using the same catalytic phase. The dodecene conversion rate calculated from chromatographic determination for each of the three successive runs is respectively 98, 97 and 95%. The three hydrocarbon phases are collected, washed, dried and distilled. There are recovered 1.8 g of dodecene, 62 g of monododecylbenzene and 4.5 g of heavy products containing didodecylbenzenes and dodecene dimers.

The 2-phenyl-dodecane content of the phenyldodecanes is 35%. The molar selectivity to monododecylbenzene with respect to the converted dodecene is 87%.

EXAMPLE 22

50 cc of a solution of SbF$_5$ and HF in sulfolane at individual concentrations of 0.1 mole per liter, and a mixture of 23.4 g of benzene and 16.8 g of 1-dodecene are introduced into a reaction vessel. The reaction is conducted at 70° C and at the atmospheric pressure with the use of a stirrer operated at 2,700 runs per minute. After 2 hours of reaction, stirring is discontinued and the settled hydrocarbon phase is withdrawn. This operation is repeated once more by using the same catalytic phase. The dodecene conversion rates estimated by chromatographic determination for both runs are respectively 95 and 90%. The two hydrocarbon phases are collected together, washed, dried and distilled. There are recovered 2.7 g of dodecene, 34.4 g of monododecylbenzene and 5.1 g of heavy products containing didodecylbenzenes and dodecene dimers. The 2-phenyl-dodecane content of the phenyldodecanes is 32%. The molar selectivity to monododecylbenzene with respect to the converted dodecene is 76%.

EXAMPLE 23

A solution containing 1.6% by weight of boron trifluoride and 0.44% by weight of hydrofluoric acid in tetramethylene sulfone is employed under the same conditions as in Example 1. Propylene is introduced continuously into the reactor at atmospheric pressure. In this way, there are obtained oligomers which separate out from the solution at a rate of about 10 g per hour per gram of boron trifluoride. These oligomers are composed of 30% dimers, 60% trimers, and 10% higher oligomers.

EXAMPLE 24

A solution containing 3% by weight of boron trifluoride and 0.32% by weight of hydrofluoric acid in tetramethylene sulfone is employed at 60° C to oligomerize a $C_3$-$C_4$ cut. The reaction is conducted under pressure in order to maintain the cut in the liquid phase. The composition of the cut in percent by weight is as follows: propane (12%), propylene (22%), isobutane (18%), n-butane (10%), isobutene (10%), 1-butene (8%), trans-2-butene (10%), cis-2-butene (9%), isopentane (1%). At a conversion rate equal to about 80% of the olefins, the resultant product contains the following oligomers: $C_6$ (10%), $C_7$ (22%), $C_8$ (43%), $C_9$ (15%), and over $C_9$ (10%).

EXAMPLES 25 TO 32

The following examples are conducted under the same reaction conditions as in Example 1. The catalyst is a Bronsted acid utilized either alone or in the presence of a metal halide. The resultant oligomers contain from 50–80% by weight of dimers and 15–40% by weight of trimers. The results set forth in the table below demonstrate how the activity of the catalysts in a solution of sulfone is affected by the nature of the specific Bronsted acid employed.

| Ex. No | Metal halide | Bronsted acid | Concentration (a) | Sulfone | Oligomers g/h/g of Bronsted acid |
|---|---|---|---|---|---|
| 25 | None | 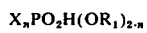 CH$_3$—⟨  ⟩—SO$_3$H | 0.4 | Sulfolane | 4 |
| 26 | None | CH$_3$SO$_3$H | 0.3 | 3-Methyl-sulfolane | 5 |
| 27 | None | CF$_3$SO$_3$H | 0.2 | (b) | 20 |
| 28 | BF$_3$ | CH$_3$COOH | 0.1 | (c) | 100 |
| 29 | BF$_3$ | CF$_3$COOH | 0.01 | (d) | 80 |
| 30 | BF$_3$ | H$_2$PO$_3$F | 0.01 | Sulfolane | 150 |
| 31 | BF$_3$ | HSO$_3$F | 0.01 | Sulfolane | 220 |
| 32 | BF$_3$ | HPO$_2$F$_2$ | 0.01 | Sulfolane | 450 |

(a) Concentration in mols per liter of each of the components of the catalyst
(b) 3,4-dichloro tetramethylene sulfone
(c) Mixture of 20% diphenylsulfone and 80% sulfolane
(d) Mixture of 60% dimethylsulfone and 40% sulfolane From the foregoing description, one skilled in the art can easily ascertain the essential characteristics of this invention and, without departing from the spirit and scope thereof, can make various changes and modifications of the invention to adapt it to various usages and conditions. Consequently, such changes and modifications are properly, equitably and intended to be within the full range of equivalence of the following claims.

What is claimed is:

1. A process for the oligomerization of a mono alpha-ethylenically unsaturated lower aliphatic hydrocarbon to predominantly dimers and trimers thereof which comprises oligomerizing the unsaturated hydrocarbon in the presence of a liquid catalyst consisting essentially of:
   a. a catalytic amount of a Bronsted acid selected from the group consisting of sulfuric acid; fluorosulfuric acid; a sulfonic acid of the formula R—SO$_3$H wherein R is alkyl, aromatic, halogenated alkyl or halogenated aromatic; HF; an acid of the formula

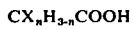
   $$X_nPO_2H(OR_1)_{2-n}$$

wherein X is a halogen, $R_1$ is a hydrogen atom or an alkyl group and $n$ is selected from 0, 1 and 2; and an acid of the formula:

$$CX_nH_{3-n}COOH$$

wherein X is a halogen and $n$ is selected from 0, 1, 2 and 3, and
   b. a sulfone of formula R''—SO$_2$—R', wherein R' and R'', taken separately, are hydrocarbon monovalent radicals containing from 1 to 8 carbon atoms or, taken together, form a hydrocarbon divalent radical containing from 3 to 12 carbon atoms, the acid catalyst concentration being between $10^{-5}$ moles per liter of sulfone and the concentration corresponding to the saturation, without exceeding 5 moles per liter, said liquid catalyst being a liquid phase distinct from the hydrocarbon phase.

2. A process according to claim 1, said catalyst further consisting essentially of a Lewis acid, the molar ratio between the Lewis acid and the Bronsted acid being 0.01 : 1 to 200 : 1, respectively.

3. A process according to claim 2, the molar ratio between the Lewis acid and the Bronsted acid being 0.1 : 1 to 10 : 1, respectively.

4. A process according to claim 1, said liquid catalyst further containing phosphoric anhydride.

5. A process for the oligomerization of a mono alpha-ethylenically unsaturated lower aliphatic hydrocarbon to predominantly dimers and trimers thereof which comprises oligomerizing the unsaturated hydrocarbon in the presence of a liquid catalyst consisting essentially of catalytic quantities of:
   a. a Lewis acid; and
   b. a co-catalyst selected from the group consisting of water; sulfuric acid; fluorosulfuric acid; a sulfonic acid of the formula R-SO$_3$H wherein R is alkyl, aromatic, halogenated alkyl or halogenated aromatic; a hydrogen halide; an acid of the formula:

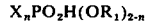
   $$X_nPO_2H(OR_1)_{2-n}$$

wherein X is a halogen, $R_1$ is a hydrogen atom or an alkyl group and $n$ is selected from 0, 1 and 2; and an acid of the formula:

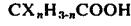
   $$CX_nH_{3-n}COOH$$

wherein X is a halogen and $n$ is selected from 0, 1, 2 and 3, the molar ratio between the Lewis acid and the co-catalyst being 0.1 : 1 to 10 : 1, respectively, and
   c. a sulfone of formula R''-SO$_2$-R', wherein R'' and R', taken separately, are hydrocarbon monovalent radicals containing from 1 to 8 carbon atoms, or taken together, form a hydrocarbon divalent radical containing from 3 to 12 carbon atoms, the acid catalyst concentration being between $10^{-5}$ moles per liter of sulfone and the concentration corresponding to the saturation, without exceeding 5 moles per liter, said liquid catalyst being a liquid phase distinct from the hydrocarbon phase.

6. A process according to claim 5, said liquid catalyst further containing phosphoric anhydride.

7. A process according to claim 5, wherein said Lewis acid is $PF_5$.

8. A process according to claim 1, said catalyst composition further containing an inert hydrocarbon solvent.

9. A process according to claim 1 wherein said unsaturated hydrocarbon is isobutene or methylbutene.

10. A process according to claim 1 wherein said unsaturated hydrocarbon is propylene.

11. A process according to claim 2 wherein said Lewis acid is a metal halide selected from the group consisting of $WF_6$, $SnCl_4$, $TiF_4$, $AlF_3$, $SnF_4$, $BF_3$, $TaF_5$, $PF_5$, and $SbF_5$.

12. A process according to claim 2, said catalyst consisting essentially of HF and $SbF_5$.

13. A process according to claim 1, said hydrocarbon being isobutene.

14. A process according to claim 2, said catalyst consisting essentially of $BF_3$ and an acid of the formula $X_nPO_2H(OR)_{2-n}$ wherein X is halogen, R is either H or alkyl, and $n$ is either 0, 1 or 2.

* * * * *